(12) United States Patent
Kassab

(10) Patent No.: US 11,266,310 B2
(45) Date of Patent: Mar. 8, 2022

(54) DEVICES, SYSTEMS, AND METHODS TO TREAT HYPERTENSION

(71) Applicant: Ghassan S. Kassab, La Jolla, CA (US)

(72) Inventor: Ghassan S. Kassab, La Jolla, CA (US)

(*) Notice: Subject to any disclaimer, the term of this patent is extended or adjusted under 35 U.S.C. 154(b) by 549 days.

(21) Appl. No.: 15/495,093

(22) Filed: Apr. 24, 2017

(65) Prior Publication Data

US 2017/0303850 A1  Oct. 26, 2017

Related U.S. Application Data

(60) Provisional application No. 62/326,818, filed on Apr. 24, 2016.

(51) Int. Cl.
| | |
|---|---|
| *A61B 5/00* | (2006.01) |
| *A61B 5/02* | (2006.01) |
| *A61B 5/0538* | (2021.01) |
| *A61B 18/14* | (2006.01) |
| *G16H 50/30* | (2018.01) |
| *G16H 50/70* | (2018.01) |
| *A61B 18/00* | (2006.01) |

(52) U.S. Cl.
CPC ........ *A61B 5/0036* (2018.08); *A61B 5/02007* (2013.01); *A61B 5/0538* (2013.01); *A61B 5/7275* (2013.01); *A61B 18/1492* (2013.01); *G16H 50/30* (2018.01); *G16H 50/70* (2018.01); *A61B 2018/00404* (2013.01); *A61B 2018/00511* (2013.01); *A61B 2018/00577* (2013.01)

(58) Field of Classification Search
None
See application file for complete search history.

(56) References Cited

U.S. PATENT DOCUMENTS

| | | | | |
|---|---|---|---|---|
| 5,054,493 | A * | 10/1991 | Cohn | A61B 5/021 600/485 |
| 5,830,131 | A * | 11/1998 | Caro | A61B 5/02108 600/300 |
| 8,099,161 | B2 * | 1/2012 | Kassab | A61B 5/053 600/547 |
| 2009/0182287 | A1 * | 7/2009 | Kassab | A61B 5/02007 604/264 |
| 2014/0012133 | A1 * | 1/2014 | Sverdlik | A61B 5/4848 600/438 |

OTHER PUBLICATIONS

Herwaarden, J. A., et al. . Dynamic magnetic resonance angiography of the aneurysm neck: Conformational changes during the cardiac cycle with possible consequences for endograft sizing and future design. (2006). Journal of Vascular Surgery, 44(1), 22-28. doi:10.1016/j.jvs.2006.03.028 (Year: 2006).*

M. Mokhtari-Dizaji, M. Montazeri, H. Saberi. "Differentiation of mild and severe stenosis with motion estimation in ultrasound images." Ultrasound Med Biol, 32 (2006), pp. 1493-1498 (Year: 2006).*

* cited by examiner

*Primary Examiner* — Matthew Kremer
*Assistant Examiner* — Samuel C Kim
(74) *Attorney, Agent, or Firm* — William F. Ward

(57) ABSTRACT

Devices, systems, and methods to treat hypertension. In at least one embodiment of a method of the present disclosure, the method comprises the step of obtaining data indicative of a renal artery of a patient with hypertension; and if the data indicates that the renal artery is stiff, relatively stiff, non-compliant, or relatively noncompliant, the method further comprises the step of performing a renal ablation procedure on the renal artery to treat the hypertension.

12 Claims, 3 Drawing Sheets

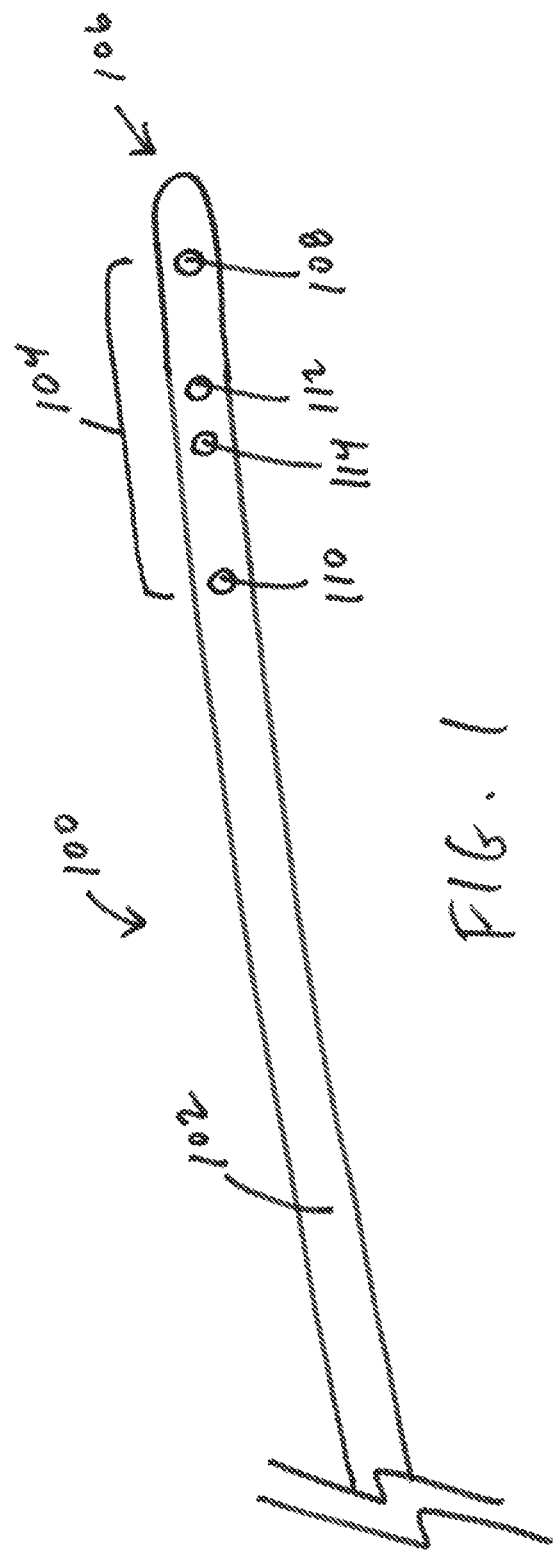
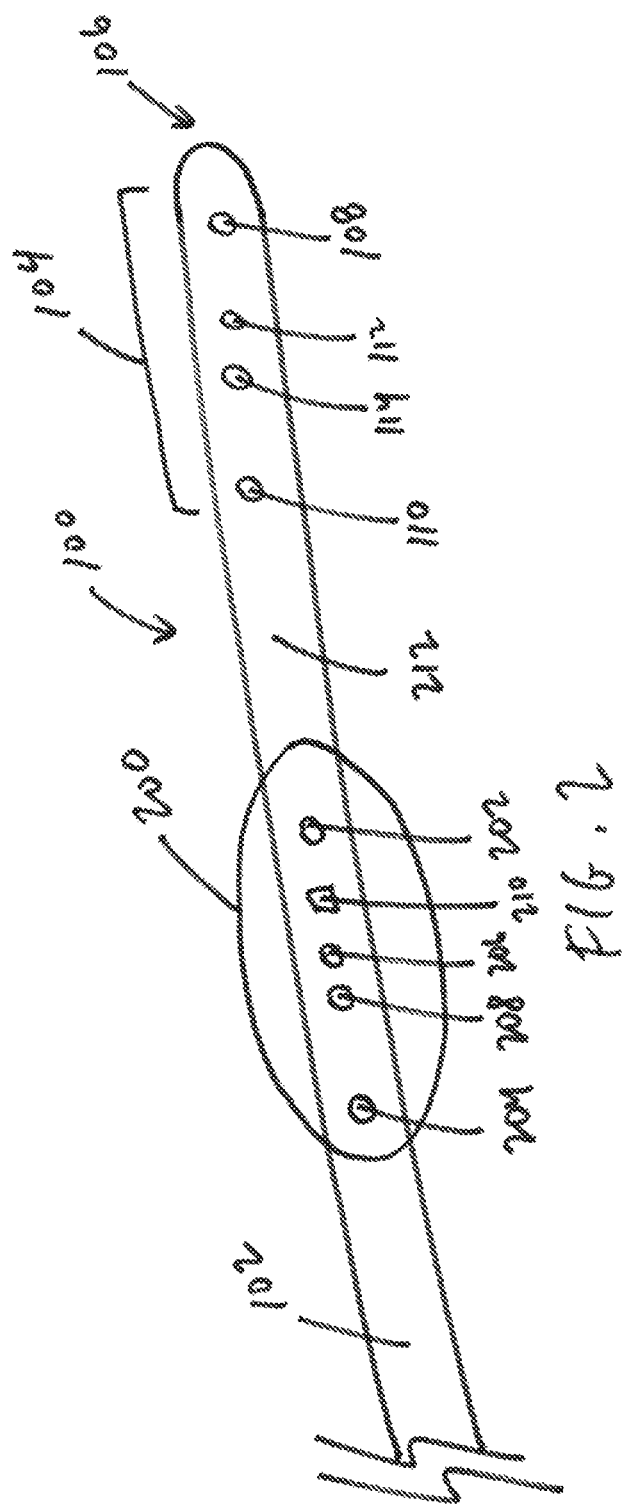

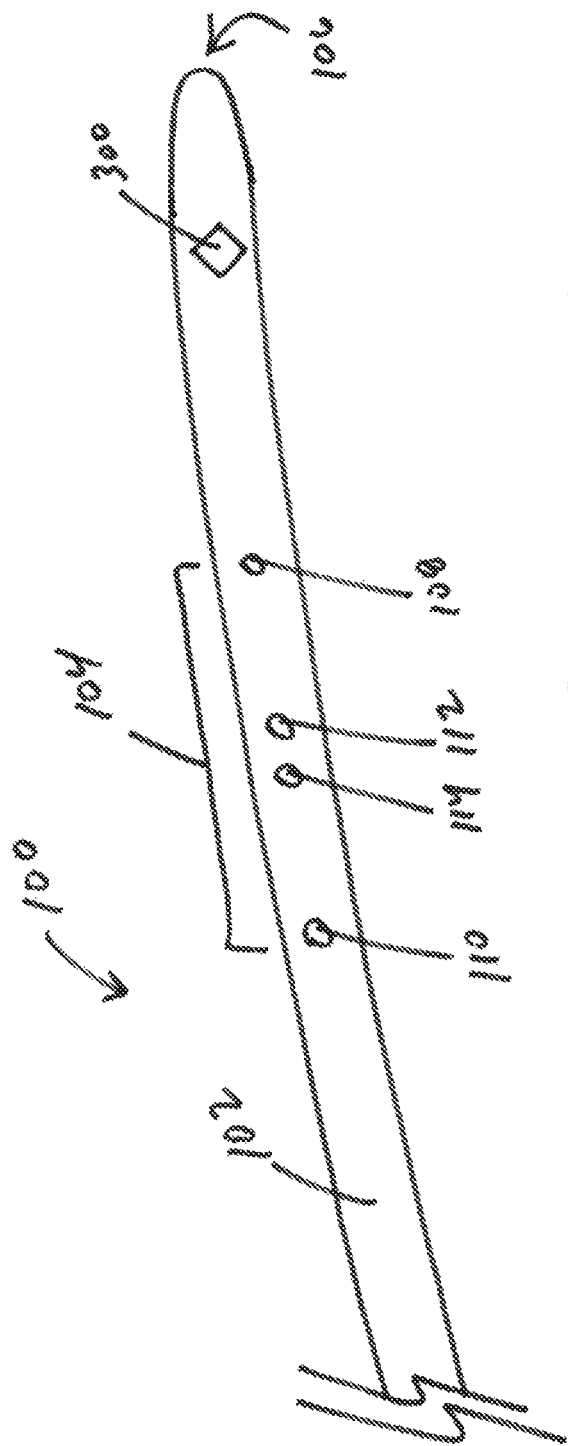
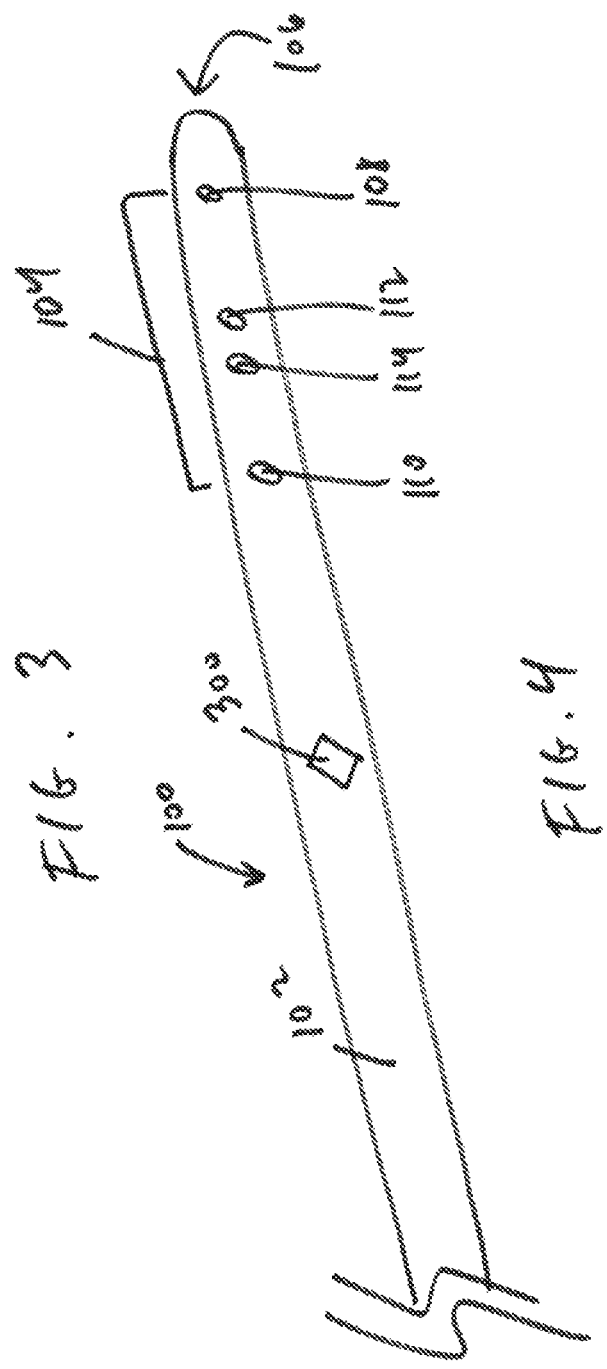

DEVICES, SYSTEMS, AND METHODS TO TREAT HYPERTENSION

PRIORITY, RELATED PATENT(S) AND PATENT APPLICATION(S), AND INCORPORATION BY REFERENCE

The present application is related to, and claims the priority benefit of, U.S. Provisional Patent Application Ser. No. 62/326,818, filed Apr. 24, 2016, the contents of which are incorporated herein by reference in their entirety.

The present application is also related to, and incorporates the entire contents of herein, the following patent(s) and patent application(s):

U.S. Pat. No. 8,099,161 to Kassab, issued Jan. 17, 2012, and all priority patents and patent applications thereto;

U.S. Pat. No. 8,185,194 to Kassab, issued May 22, 2012, and all priority patents and patent applications thereto; and U.S. patent application Ser. No. 14/521,148 of Kassab et al., filed Oct. 22, 2014, and all priority patent applications thereto.

BACKGROUND

Hypertension (high blood pressure) affects nearly 100 million people in the United States alone. Approximately 1% of that group do not react to pharmacological treatment.

Within that subgroup, treatment via renal ablation to treat hypertension is a potential option. Renal ablation (also referred to as renal denervation) is a procedure whereby ablative energy, such as radiofrequency energy, is directed toward portions of the renal artery in attempt to ablate portions thereof to address overactivity of the renal sympathetic nervous system. However, it has been discovered that a significant percentage (approximately 30-35%) of renal ablation patients don't respond either (i.e., non-responders). Hence, it would be ideal to have a method that predicts responders from non-responders to optimize the outcome of renal ablation only to those patients that are likely to benefit from the therapy.

In view of the same, improved renal ablation methods, and devices and systems useful to perform the same, would be well received in the marketplace.

BRIEF SUMMARY

In at least one embodiment of a method of the present disclosure, the method comprises the step of obtaining data indicative of a renal artery of a patient with hypertension; and if the data indicates that the renal artery is stiff, relatively stiff, noncompliant, or relatively noncompliant, the method further comprises the step of performing a renal ablation procedure on the renal artery to treat the hypertension.

In at least one embodiment of a method of the present disclosure, the data comprises compliance, stiffness, or pulsatility data.

In at least one embodiment of a method of the present disclosure, the data comprises at least two of compliance data, stiffness data, and pulsatility data.

In at least one embodiment of a method of the present disclosure, the step of obtaining data is performed using a detector of an impedance device.

In at least one embodiment of a method of the present disclosure, the impedance device comprises an impedance wire.

In at least one embodiment of a method of the present disclosure, the impedance device comprises an impedance catheter.

In at least one embodiment of a method of the present disclosure, the step of performing the renal ablation procedure is performed using an ablation element of the impedance device.

In at least one embodiment of a method of the present disclosure, the step of obtaining data is performed by obtaining real-time impedance measurements within the renal artery, determining cross-sectional areas of the renal artery based upon the real-time impedance measurements, and determining an index of pulsatility based upon the cross-sectional areas as relating to a cardiac cycle of the patient.

In at least one embodiment of a method of the present disclosure, the data indicates that the renal artery is stiff, relatively stiff, noncompliant, or relatively noncompliant if the index of pulsatility is at or above 5%.

In at least one embodiment of a method of the present disclosure, the data indicates that the renal artery is stiff, relatively stiff, noncompliant, or relatively noncompliant if the index of pulsatility indicates that the renal artery has a change in cross-sectional area of at or greater than 10%.

In at least one embodiment of a method of the present disclosure, the method comprises the step of obtaining data indicative of a renal artery of a patient with hypertension, the data selected from the group consisting of compliance data, stiffness data, and pulsatility data; and performing a renal ablation procedure on the renal artery to treat the hypertension if the data indicates that the renal artery is at or above a threshold level of stiffness or noncompliance.

In at least one embodiment of a method of the present disclosure, the data comprises at least two of compliance data, stiffness data, and pulsatility data.

In at least one embodiment of a method of the present disclosure, the step of obtaining data is performed using a detector of an impedance device.

In at least one embodiment of a method of the present disclosure, the impedance device comprises an impedance wire.

In at least one embodiment of a method of the present disclosure, the impedance device comprises an impedance catheter.

In at least one embodiment of a method of the present disclosure, the step of performing the renal ablation procedure is performed using an ablation element of the impedance device.

In at least one embodiment of a method of the present disclosure, the method comprises the step of obtaining compliance, stiffness, or pulsatility data of a renal artery of a patient with hypertension; and if the compliance or pulsatility data indicates that the renal artery is stiff, relatively stiff, noncompliant, or relatively noncompliant, performing a renal ablation procedure on the renal artery to treat the hypertension of the patient.

In at least one embodiment of a method of the present disclosure, the step of obtaining data is performed by obtaining real-time impedance measurements within the renal artery, determining cross-sectional areas of the renal artery based upon the real-time impedance measurements, and determining an index of pulsatility based upon the cross-sectional areas as relating to a cardiac cycle of the patient, and wherein the data indicates that the renal artery is stiff, relatively stiff, noncompliant, or relatively noncompliant if the index of pulsatility is at or above 5%.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIGS. 1-4 show distal portions of impedance devices, according to exemplary embodiments of the present disclosure;

Figure 6:
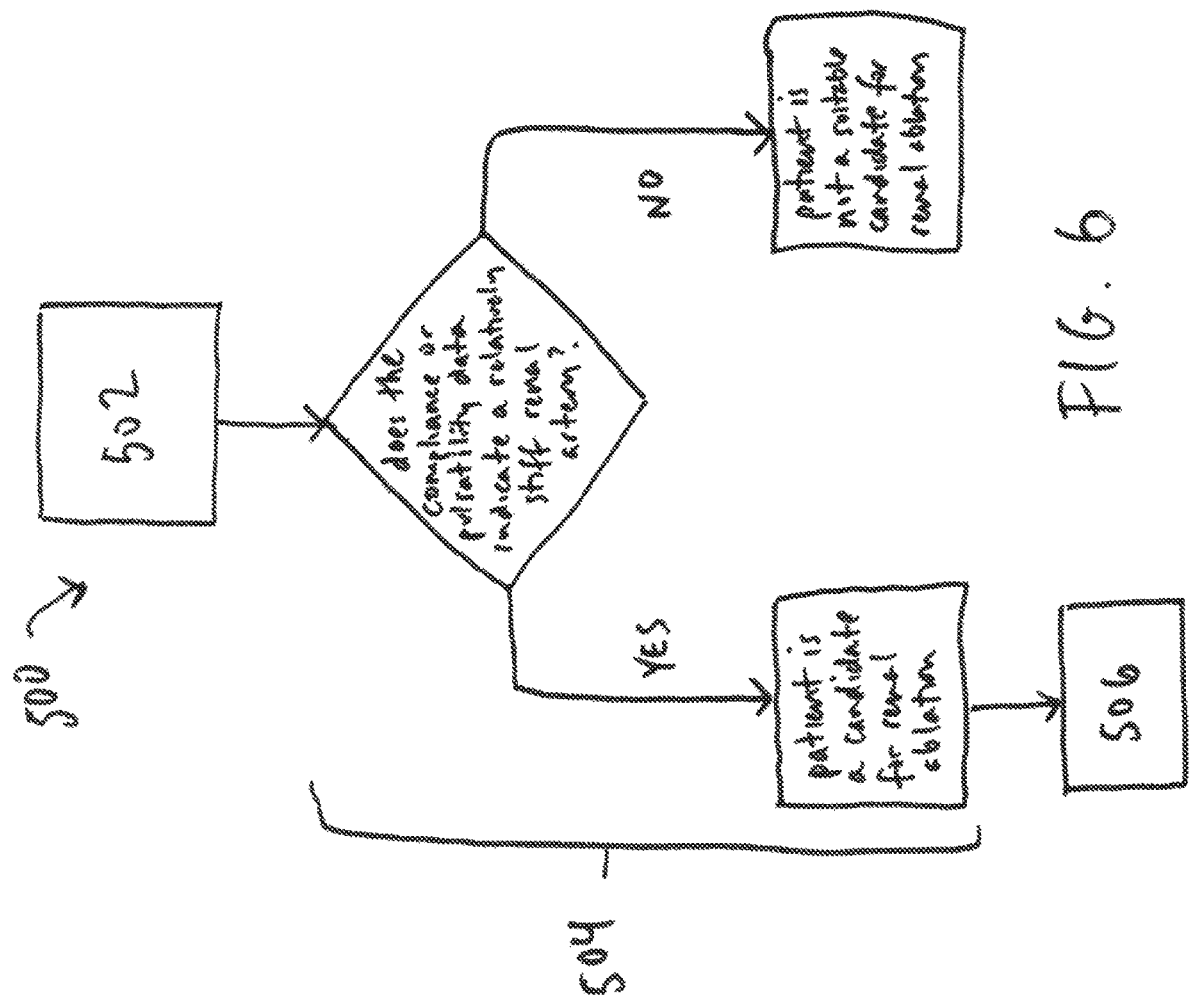
FIG. 6 shows a method of patient treatment in flowchart format, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure includes disclosure of methods, and devices and systems to perform the same, to address problems with current technology/methods for treating hypertension using renal ablation.

The present disclosure includes disclosure of an exemplary method, comprising obtaining information relating to the compliance of the renal artery in conjunction with a potential renal ablation procedure to treat hypertension. As described herein, the present disclosure includes disclosure that identifies that a relatively stiffer renal artery is likely to respond better to renal ablation, such as due to a greater sympathetic drive, versus a more compliant or pulsatile renal artery. As such, one or more measurements of renal artery compliance or pulsatility, as identified in various methods herein, can be obtained, and the smaller the number, the higher likelihood of a positive response to renal ablation to treat hypertension.

A neural component fires into the renal artery, and it has been determined that firing neurons into the renal artery affects its basal tone. If there is insignificant firing at the renal artery, the mechanism of hypertension is not because of renal access—the hypertension is caused by something else.

As noted above, the disclosure of the present application includes disclosure that patients with relatively stiffer renal arteries react better to renal ablation treatments versus patients with relatively less stiff renal arteries. In view of the same, and prior to the potential performance of a renal ablation therapy, renal artery compliance or pulsatility of a patient should be determined/measured, and based on the outcome of such a determination/measurement, a subsequent determination of whether or not to treat the patient using renal ablation can be made.

In at least one method of the present disclosure, an impedance device is used to obtain a renal artery compliance or pulsatility measurement. Said impedance devices, and general methods to determine vessel compliance using said impedance devices, may be as described within U.S. Pat. No. 8,099,161 to Kassab, the contents of which are incorporated herein in their entirety.

Impedance devices 100 of the present disclosure may be as shown in FIGS. 1-4. As shown in FIG. 1, for example, an exemplary impedance device 100 comprises an elongated body 102, with a distal portion of elongated body 102 shown in the figure. An impedance detector 104 is positioned and/or located along elongated body 102, such as at or near a distal tip 106 of elongated body 102. Impedance detector 104 can comprise one or more electrodes, such as a first excitation electrode 108, a second excitation electrode 110, a first detection electrode 112, and/or a second detection electrode 114. Additional electrodes may be used in various embodiments. FIG. 1 represents an exemplary wire embodiment of an impedance device 100 of the present disclosure. In use, for example, first excitation electrode 108 and second excitation electrode 110 may be activated to generate an electric field within a mammalian luminal organ, with said electric field detected using the first detection electrode 112 and the second detection electrode 114, in an embodiment of an impedance device 100 that uses said electrodes 108, 110, 112, 114. In other embodiments, at least one excitation electrode (108 and/or 110) and at least one detection electrode (112 and/or 114) would be positioned or located on or along impedance device 100, and at least another excitation electrode and at least another detection electrode would be positioned somewhere else, such as upon a second impedance device, a patch on the skin, an internal device, etc., so that the generated electric field can be detected as described above and within U.S. Pat. No. 8,099,161 to Kassab.

An additional impedance device 100 embodiment of the present disclosure is shown in FIG. 2. As shown therein, which depicts an exemplary catheter embodiment, impedance device 100 can comprise the same or different electrodes 108, 110, 112, 114, and may also optionally comprise a balloon 200 with additional electrodes therein, such as a first balloon excitation electrode 202, a second balloon excitation electrode 204, a first balloon detection electrode 206, and/or a second balloon detection electrode 208. Balloon 200 can be inflated or deflated via a gas and/or a liquid from within impedance device, such as via balloon port 210 in communication with a lumen 212 of impedance device. In use, for example, first balloon excitation electrode 202 and second balloon excitation electrode 204 may be activated to generate an electric field within balloon 200, with said electric field detected using the first balloon detection electrode 206 and the second balloon detection electrode 208, in an embodiment of an impedance device 100 that uses said electrodes 202, 204, 206, 208.

FIGS. 3 and 4 show additional device 100 embodiments, including a detector 104, for example, and an ablation element 300, shown as being distal to detector 104 in FIG. 3 and proximal to detector 104 in FIG. 4. As referenced herein, ablation element 300 is operable to deliver ablative energy to the renal artery to ablate the same, as desired. Systems of the present disclosure may comprise one or more devices 100 and one or more other components, such as shown within FIG. 3 of U.S. Pat. No. 8,099,161 to Kassab and described therein.

The novelty with respect to the present disclosure is, at least in part, a method of treating a patient by way of determining renal artery compliance, such as by using an impedance device 100 of the present disclosure or another device or system useful to determine renal artery compliance, prior to actually performing a renal ablation procedure. Exemplary impedance devices 100 of the present disclosure can measure renal artery compliance in real time, such as by way of obtaining impedance measurements within the renal artery and using said impedance measurements to determine local cross-sectional area measurements within the renal artery, in real time. These cross-sectional areas (CSAs) can be measured along with the patient's cardiac cycle, and an index of pulsatility can then be determined. For example, if the renal artery is truly rigid or stiff, the compliance would be at or near zero.

If the renal artery instead moves a significant amount, such as by way of 5%, 10%, or some other measurable percentage above a nominal percentage, that would be indicative of a relatively compliant or pulsatile renal artery. A healthy renal artery, namely a compliant renal artery, may have a 10% (or at or near 10%) or greater change in CSA during a cardiac cycle, and therefore would be indicative of a renal artery that would not be particularly suitable for a renal ablation procedure.

As noted above, a less compliant renal artery is a better candidate for a renal ablation procedure. More parasympathetic firing causes smooth muscle to contract, and therefore result in a less compliant renal artery. A stiffer renal artery is therefore a better candidate for a renal ablation treatment, as a higher incidence of neural firing is associated with hypertension in certain instances.

U.S. patent application Ser. No. 14/521,148 of Kassab et al., describes the use of impedance devices to obtain conductance measurements, and also describes methods that use said devices to obtain conductance measurements and to subsequently perform a medical procedure. One such medical procedure is renal ablation to treat hypertension. However, the specific mechanism as to when or why to perform a renal ablation procedure to treat hypertension is provided in further detail within the present disclosure, and as noted above, relates to renal artery compliance.

Figure 5:
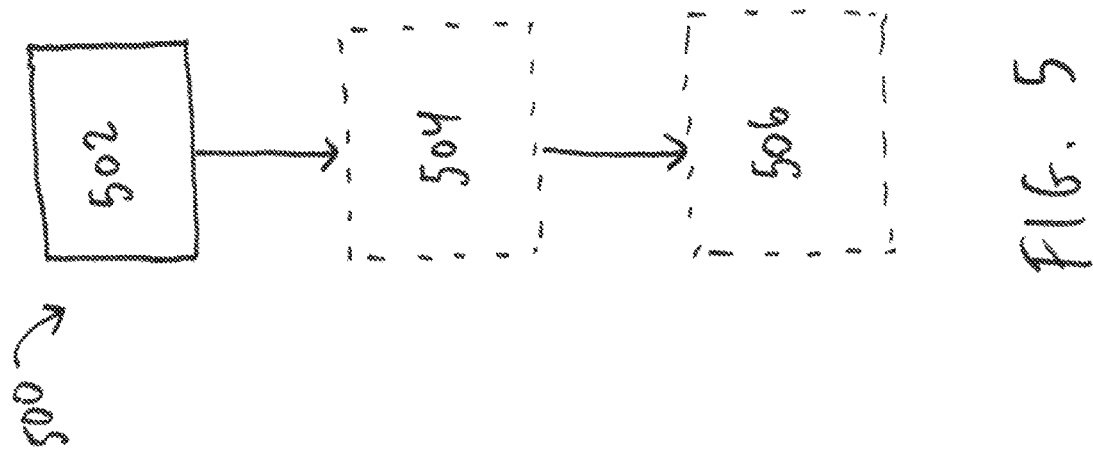
FIG. 5 shows a method of patient treatment in box step format, according to an exemplary embodiment of the present disclosure.

In view of the foregoing, at least one method of the present disclosure includes the steps shown in box step format in FIG. 5. As shown therein, method 500 comprises the step of obtaining renal artery compliance or pulsatility data (data step 502), using, for example, a device 100 of the present disclosure. Said compliance or pulsatility data can be obtained, for example, as referenced within U.S. Pat. No. 8,099,161 to Kassab and/or U.S. Pat. No. 8,185,194 to Kassab. Device 100 can be operated within the renal artery using conductance, whereby impedance measurements are obtained in connection with the cardiac cycle to obtain the compliance or pulsatility data.

Method 500, in at least one embodiment, further comprises the step of comparing the compliance or pulsatility data obtained in data step 502 to threshold data to determine whether or not the patient is suitable for a renal ablation procedure (comparison step 504). For example, the threshold data may be a particular percentage of compliance or pulsatility, a range of compliance or pulsatility, a percentage change of cross-sectional area, a range of changes in cross-sectional area, etc., that if met or potentially exceeded, would indicate that the patient is not suitable for a renal ablation procedure, as such a procedure would likely not be effective to treat hypertension for that particular patient. For example, threshold data may be, for example, a 5% compliance or pulsatility change, a 10% compliance or pulsatility change, etc., and if the compliance or pulsatility data obtained in data step 502 is below said percentages, that would indicate, by way of comparison step 504, that the patient would be a candidate for a renal ablation procedure. Comparison step 504 is shown as being optional in FIG. 5, as the comparison step 504 may essentially be performed concurrent with data step 502, as, for example, data obtained in data step 502 could itself indicate whether or not the patient is suitable for a renal ablation procedure. Should the patient be suitable for a renal ablation procedure, by way of identifying a relatively stiff renal artery via steps 502 and/or 504, a renal ablation procedure could then be performed (renal ablation procedure step 506). Step 506 is also shown as optional, as should a patient not be suitable for a renal ablation procedure, such as by way of a relatively compliant or pulsatile renal artery via steps 502 and/or 504, step 506 would not be performed. FIG. 6 indicates a similar method but within flowchart format to assist with understanding said concept, identifying that a renal ablation procedure step 506 can be performed in the patient is a candidate for renal ablation.

Step 504 (or essentially step 502, as noted above) could be performed to identify an index of compliance or pulsatility as defined below:

$$(D_s-D_d)/D_d$$

wherein $D_s$ is a renal artery diameter during systole, and $D_d$ is a renal artery diameter during diastole, for example. If cross-sectional areas are determined, an index of compliance or pulsatility is defined as:

$$(CSA_s-CSA_d)/CSA_d$$

wherein $CSA_s$ is a renal artery cross-sectional area during systole, and $CSA_d$ is a renal artery cross-sectional area during diastole, for example. Such indices could, for example, comprise the compliance or pulsatility data obtained in data step 502 as noted above. A normal compliance (index) of a blood vessel is around 10-15% change in diameter. This degree of compliance would not be a good candidate for renal ablation. An index of zero value indicates a perfectly stiff vessel (i.e., no change in diameter or CSA) and hence would be the most likely candidate for renal ablation. The cutoff for clinical intervention can be determined through clinical trials.

Renal ablation procedure step 506 can be performed using traditional ablative procedures, such as by using a medical device that is not device 100, or, in at least some embodiments, could be performed using device 100, such as shown in FIGS. 3 and 4. If using device 100, detector 104 could be used to obtain the compliance or pulsatility data obtained in data step 502, and ablation element 300 could be used to deliver the ablation energy to ablate the renal artery within renal ablation procedure step 506.

While various embodiments of method to treat hypertension and devices and systems to perform the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method, comprising the step of:
obtaining data indicative of a renal artery of a patient with hypertension using an impedance catheter positioned within the renal artery of the patient, wherein the data is obtained before an initial renal ablation procedure, wherein the data is obtained by performing real-time impedance measurements within the renal artery, determining cross-sectional areas of the renal artery based upon the real-time impedance measurements, and determining an index of pulsatility based upon the cross-sectional areas as relating to a cardiac cycle of the patient;
determining if the patient should be treated with the initial renal ablation procedure based on a determination of whether the data indicates that the renal artery is stiff, relatively stiff, noncompliant, or relatively noncompliant when the index of pulsatility is at, or less than, 10%;
if the data indicates that the renal artery is stiff, relatively stiff, noncompliant, or relatively noncompliant when the index of pulsatility is at, or less than, 10%, the method further comprises the step of:
performing the initial renal ablation procedure on the renal artery in real-time using an ablation element of the impedance catheter to treat the hypertension, while the impedance catheter is still positioned within the rental artery of the patient.

2. The method of claim 1, wherein the data comprises compliance data.

3. The method of claim 1, wherein the data comprises stiffness data.

4. The method of claim 1, wherein the data comprises pulsatility data.

5. The method of claim 1, wherein the data comprises at least two of compliance data, stiffness data, and pulsatility data.

6. The method of claim 1, wherein the step of obtaining data is performed using a detector of the impedance catheter.

7. The method of claim 1, wherein the data indicates that the renal artery is stiff, relatively stiff, noncompliant, or relatively noncompliant when the index of pulsatility is at, or below, 5%.

8. A method, comprising the step of:
obtaining data indicative of a renal artery of a patient with hypertension, the data selected from the group consisting of compliance data, stiffness data, and pulsatility data, wherein the data is obtained before an initial renal ablation procedure, wherein the data is obtained using an impedance catheter positioned within the renal artery of the patient by performing real-time impedance measurements within the renal artery, determining cross-sectional areas of the renal artery based upon the real-time impedance measurements, and determining an index of pulsatility based upon the cross-sectional areas as relating to a cardiac cycle of the patient; and
performing the initial renal ablation procedure on the renal artery in real-time using an ablation element of the impedance catheter to treat the hypertension after determining if the patient should be treated with ablation;
wherein the patient should be treated with the initial renal ablation procedure when if the index of pulsatility is at, or below threshold level of 10%.

9. The method of claim 8, wherein the data comprises at least two of the compliance data, the stiffness data, and the pulsatility data.

10. The method of claim 8, wherein the step of obtaining data is performed using a detector of the impedance catheter.

11. A method, comprising the step of obtaining compliance, stiffness, or pulsatility data of a renal artery of a patient with hypertension, wherein the data is obtained before an initial renal ablation procedure, wherein the data is obtained using an impedance catheter positioned within the renal artery of the patient by performing real-time impedance measurements within the renal artery, determining cross-sectional areas of the renal artery based upon the real-time impedance measurements, and determining an index of pulsatility based upon the cross-sectional areas as relating to a cardiac cycle of the patient, and wherein the data indicates that the renal artery is stiff, relatively stiff, noncompliant, or relatively noncompliant when the index of pulsatility is at, or below, 10%;
if the compliance, stiffness, or pulsatility data indicates that the renal artery is stiff, relatively stiff, noncompliant, or relatively noncompliant
performing the initial renal ablation procedure on the renal artery in real-time to treat the hypertension of the patient, while the impedance catheter is still positioned within the rental artery of the patient.

12. The method of claim 11, wherein the data indicates that the renal artery is stiff, relatively stiff, noncompliant, or relatively noncompliant if the index of pulsatility is at, or below, 5%.

* * * * *